(12) United States Patent
Forster (10) Patent No.: US 11,607,237 B2
(45) Date of Patent: Mar. 21, 2023

(54) GEAR ARRANGEMENT AND SURGICAL INSTRUMENT WITH A GEAR ARRANGEMENT

(71) Applicant: KARL STORZ SE & Co. KG, Tuttlingen (DE)

(72) Inventor: Jonas Forster, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 271 days.

(21) Appl. No.: 17/132,740

(22) Filed: Dec. 23, 2020

(65) Prior Publication Data

US 2021/0113228 A1    Apr. 22, 2021

Related U.S. Application Data

(62) Division of application No. 16/026,225, filed on Jul. 3, 2018, now Pat. No. 10,905,450.

(30) Foreign Application Priority Data

Jul. 4, 2017    (DE) .................... 10 2017 114 838.8

(51) Int. Cl.
*A61B 17/29* (2006.01)
*A61B 17/3201* (2006.01)
*A61B 17/28* (2006.01)
*A61B 17/32* (2006.01)

(52) U.S. Cl.
CPC .......... *A61B 17/29* (2013.01); *A61B 17/3201* (2013.01); *A61B 17/320016* (2013.01); *A61B 2017/2808* (2013.01); *A61B 2017/2919* (2013.01); *A61B 2017/2923* (2013.01); *A61B 2017/2927* (2013.01); *A61B 2017/2938* (2013.01); *A61B 2017/2939* (2013.01)

(58) Field of Classification Search
CPC .... A61B 2017/2919; A61B 2017/2923; A61B 2017/2927; A61B 2017/2938; A61B 2017/2939; A61B 2017/2926; A61B 2017/2932; A61B 2017/2933; A61B 17/29

See application file for complete search history.

(56) References Cited

U.S. PATENT DOCUMENTS

2017/0071617 A1\* 3/2017 Kawaguchi ........ A61B 18/1442

\* cited by examiner

*Primary Examiner* — Majid Jamialahmadi
(74) *Attorney, Agent, or Firm* — McGlew and Tuttle, P.C.

(57) ABSTRACT

A gear arrangement including two drive units (210, 220, 310, 320, 410), and two translatory transmission elements (151, 152, 251, 252, 351, 352), to each of which a rotationally movable function unit (141, 142) of a distally arranged two-part end effector (140) can be coupled. The first drive unit (210, 310, 410) has at least one proximally arranged rotation element (311, 411) or a thrust element (210) for opening or closing the end effector (140) by rotation of at least one function unit (141, 142). The second drive unit (220, 320), with which the translatory transmission elements (151, 152, 251, 252, 351, 352) are movable in opposite directions, has at least one proximally arranged rotation element (224, 320, 421) for simultaneous and unidirectional pivoting of the function units (141, 142) of the end effector (140). A surgical instrument includes the gear arrangement (200, 300, 400) in the handle (180).

11 Claims, 4 Drawing Sheets

GEAR ARRANGEMENT AND SURGICAL INSTRUMENT WITH A GEAR ARRANGEMENT

CROSS REFERENCE TO RELATED APPLICATIONS

This application is a divisional under 37 CFR 1.53(b) of pending prior U.S. patent application Ser. No. 16/026,225 filed Jul. 3, 2018, which claims the benefit of priority under 35 U.S.C. § 119 of German Application DE 10 2017 114 838.8, filed Jul. 4, 2017, the entire contents of each application are incorporated herein by reference.

FIELD OF THE INVENTION

The present invention pertains to a gear arrangement and a surgical instrument with a gear arrangement.

BACKGROUND OF THE INVENTION

In minimally invasive surgery (MIS), a surgical instrument is inserted into a body through a natural opening, or through an opening created by the surgeon, in order to withdraw samples or perform interventions at predetermined locations. Hand-held instruments available for minimally invasive surgery are generally rigid. When using such rigid instruments, only a limited number of degrees of freedom are available to the surgeon.

If an end effector on the instrument head, for example in the form of forceps, scissors or grippers, is inserted into the interior of a human body, the head of a manually controlled instrument can often only be opened or closed and rotated about the longitudinal axis of the shaft, which is in most cases rod-shaped. The freedom of movement of these hand-held devices is restricted and thus also limits the maneuverability of the surgeon. A limited maneuverability may unnecessarily prolong the operation and may possibly increase the risk of the patient suffering complications.

Most of the manually guided minimally invasive instruments have too few degrees of freedom, or the instrument head and transmission mechanism is not sufficiently stable, for example in order to be able to suture or dissect with precision. In order to permit further degrees of freedom, such as pivoting of the end effector, complicated mechanical constructions are needed. The necessary mechanical gear ratio does not permit intuitive and precise control. Lack of stability and force transmission are known problems of these systems. Moreover, depending on the experience of the person operating, manual control of several degrees of freedom with mechanical instruments requires lengthy periods of training and a great deal of dexterity, such that a robot-assisted approach or the integration of electrical actuators is often preferred over manually guided instruments, in order to obtain pivoting of the functional end of the instrument.

SUMMARY OF THE INVENTION

An object of the invention is to make available an improved manually guided instrument for minimally invasive surgery. It is in particular an object to make available a surgical instrument with improved operator comfort and instrument maneuverability.

A further object of the invention is to provide the operator with a minimally invasive instrument having sufficient freedom of actuation, and having an extended working range of the instrument head, without using robotic systems, A further object of the invention is to mechanically decouple the degrees of freedom of a manually guided instrument from each other in order to provide the operator with a control element for each degree of freedom and to provide a more stable instrument geometry.

The invention is intended to overcome the abovementioned disadvantages, in particular the restricted freedom of movement of conventional mechanical instruments. The transmission of force from the drive units to a two-part end effector is intended to be optimized. Therefore, the object of the invention is to develop a mechanical, manually guided medical instrument and to make available an improved gear arrangement.

These objects are achieved by a gear arrangement according to the invention and by a surgical instrument with a gear arrangement according to the features of the main claim. Preferred embodiments such as a gear arrangement based on a whiffletree mechanism or a planetary gear transmission mechanism are included in the present invention.

According to a first aspect of the invention, a gear arrangement is made available comprising two drive units, and two translatory transmission elements, to each of which a rotationally movable function unit of a distally arranged two-part end effector can be coupled. The first drive unit has at least one proximally arranged rotation element or a thrust element for opening or closing the end effector by means of rotation of at least one function unit. The second drive unit, with which the translatory transmission elements are movable in opposite directions, has at least one proximally arranged rotation element for lateral pivoting of the end effector by means of unidirectional rotation of both function units.

In this way, as the first degree of freedom of the end effector, the opening or closing of the end effector can be actuated by means of at least one degree of freedom of a function unit with its own separate drive unit. An opening or closing of the end effector can be brought about in which at least one function unit is moved with respect to the other function unit. In an advantageous embodiment, the drive unit is configured to simultaneously rotate both function units toward each other or away from each other in order to generate, with respect to the closed position of the end effector, an opening angle which preferably comprises an angle range from 0° to 90° relative to the center axis or longitudinal axis of the transmission elements.

With the aid of the second drive unit of the gear arrangement according to the invention, a second degree of freedom, namely the lateral pivoting or kinking of the function units of the end effector, can advantageously be generated. By means of the at least one rotation element of the second drive unit, both function units of the end effector can be pivoted simultaneously and in the same direction into a pivoting angle. By the combination of the two drive units, the surgical instrument can be actuated, i.e. opened or closed, in each of the pivoted positions with the aid of a suitable control element.

By means of the second drive unit, interventions can advantageously be performed with a two-part end effector not only in the customary way in an axial orientation of the instrument shaft but also laterally thereof. In this way, the operator or a surgeon can choose between two degrees of freedom and can thus perform a minimally invasive intervention through extremely small openings.

Through the additional degree of freedom of the lateral pivoting, the maneuverability of the end effector inside the body can be improved, which represents an important improvement for applications in minimally invasive surgery.

According to a further aspect of the invention, the translatory transmission elements between the end effector and the drive units are arranged in an elongate shaft, at the proximal end of which is arranged a handle with at least one control element that can be assigned to a drive unit.

The translatory transmission elements can be configured as a pull/push rod or as a flexible element, for example a cable.

An elongated shaft is constructed specifically for minimally invasive surgery so as to be able to be inserted through extremely small body openings. A gear arrangement integrated in the handle or in the handle housing is provided at the proximal end of the so-called long shaft instrument. There is the possibility of rotating the entire gear about the axis of the instrument shaft in order to bring about a rotation of the instrument.

As a suitable control element for the pivoting drive, it is advantageously possible to provide a pivoting body that can be controlled intuitively. To simplify the control of the end effector, the respective pivoting angle of the pivoting body can be converted into a corresponding pivoting angle of the medical instrument.

According to a further aspect of the invention, a function unit of the end effector is chosen from the group comprising: grippers, scissors, clamp, jaw part, expander, and applicator forceps jaw for clips or staples.

The stated function units can be coupled in different shapes and sizes appropriate for the purpose, and for the corresponding use as gripping, clamping and/or cutting instruments, on the distal end of the transmission elements. Moreover, jaw parts can be parts of forceps or pincers and can in part additionally have a toothed profile or a textile fabric covering in order to be able to protect tissue while being able to grip it securely. Possible uses for the various function units are dissecting, cutting, gripping, lifting, retracting, holding. By means of attachment of applicator forceps or the like, the surgical instrument can be used for suturing, ligaturing, clamping or clipping or for applying staples. Said elements, which can be held by the forceps limbs, can be inserted into the body of a patient and used, for example, to clamp off vessels or the like.

According to a further aspect of the invention, the gear arrangement is based on a whiffletree mechanism and has a whiffletree which connects the transmission elements in each case in the region of their proximal end, wherein the first drive unit for opening and closing the end effector is configured as a linearly displaceable thrust element which is arranged centrally on the whiffletree in order to produce a unidirectional linear movement of both transmission elements and therefore a contradirectional rotary movement of both function units relative to each other.

The whiffletree, which can be made available in the form of a simple rod, represents a simple and cost-effective mechanism by which the respective negative or positive thrust force of the first drive unit can be transferred uniformly to both transmission elements.

According to a further aspect of the invention, the whiffletree, at at least one of its ends, is connected to the rotation element of the second drive unit via at least one connecting rod in order to transmit, in accordance with a pivoting of the rotation element configured as a rod, a drive torque to the whiffletree for the purpose of pivoting the end effector.

The whiffletree, by means of a simple right angle composed of rotation rod and connection rod, can be manually pivoted such that one limb of the preferably centrally angled whiffletree moves toward a transmission element in order to impart a positive thrust, while the other limb moves away from the other transmission element in order to exert a negative thrust. The in this case right-angled pivoting drive unit forms a pivoting body which can be controlled by hand and which is easy to control.

According to a further aspect of the invention, the whiffletree has at the center a rigid obtuse angle and, together with at least one further connection rod between the free ends of the rotation element and of the whiffletree, forms a polygonal pivotable grip piece as a control element for pivoting the end effector by means of contradirectional movements of the translatory transmission elements.

By providing connection rods on both sides of the whiffletree, a framework or polygon is formed which represents a more stable pivoting drive unit than a simple angle. In this way, the two translatory transmission elements coupled to the whiffletree can be actuated more precisely in opposite directions. The frameworks of the polygon composed of the rods of the drive unit and of the angled whiffletree preferably form a pentagon which, in the neutral position or non-pivoted basic position of the end effector, can approximate the circular arc movements of the instrument head. The polygon, rotatable about a rotation axis, can be easily gripped and controlled by the operator as a grip structure that is rotatable relative to the instrument shaft.

According to a further aspect of the invention, at least one drive unit of the gear arrangement is based on a planetary gear transmission mechanism, wherein the rotation element of the second drive unit or of the pivoting drive is configured as a sun gear that can be driven in rotation, wherein a first planet gear and a second planet gear for taking up a drive torque are in constant toothed engagement with the sun gear and resulting moments of the planet gears can be conveyed to a respective planet carrier. The transmission elements are each coupled to a planet carrier in order to be movable in opposite directions during the driving of the sun gear.

If only the pivoting drive unit is configured as a planetary gear, it is necessary to be able to move the transmission elements additionally in the same direction in order to open or close the end effector. This can be achieved by further rotation elements in the planetary gear or by a thrust element which can be coupled to the end regions of the transmission elements (as in the whiffletree mechanism). By avoiding a large number of drive elements and motors, the surgical instrument and a gear arrangement that can be integrated therein remain structurally simple, which results in lower manufacturing costs.

According to a further aspect of the invention, the sun gear can be driven in rotation directly or indirectly via a further coaxially arranged rotation element connected fixedly to the sun gear, when the sun gear or rotation element is selectively in toothed engagement with an outer toothing of a pivotable gearwheel segment of a control element.

By means of a selective toothed engagement, the operator can choose whether the sun gear runs free or is intended to function as a drive unit by means of a movement of the gearwheel segment.

According to a further aspect of the invention, the at least one rotation element of the first drive unit is configured as a first ring gear segment that can be driven in rotation, wherein the first planet gear for taking up a drive torque is in constant toothed engagement with the first ring gear segment and resulting moments of the first planet gear can be conveyed to the first planet carrier. By means of the first transmission element, the output of the first planet carrier can be converted, according to the chosen direction of drive rotation of the ring gear segment, into a positive or negative thrust for opening or closing the end effector by means of rotation of the couplable first function unit.

According to a further aspect of the invention, the first drive unit has a rotation element configured as a second ring gear segment, wherein the second planet gear for taking up a drive torque is in constant toothed engagement with the second ring gear segment, and the movement of the second planet gear can be conveyed to the second planet carrier. By means of the second transmission element, the output of the second planet carrier can be converted, according to the chosen direction of drive rotation of the ring gear segment, into a positive or negative thrust for opening or closing the end effector by means of rotation of the couplable second function unit.

By the use of several drive units or driving rotation elements in the gear arrangement, an exact and separate control of degrees of freedom is possible. On the one hand, the rotation elements configured as ring gear segments of the first drive unit can each separately control a degree of freedom of rotation of a function unit. On the other hand, a pivoting of the end effector can be brought about by the second drive unit (sun gear).

The use of a planetary gear is particularly advantageous for the precision of the medical instrument. This can optimize the force transmission by virtue of a high degree of stiffness and low circumferential backflash. In particular, precise movement patterns with a very high level of reproducibility can be guaranteed. This is a precondition for precise operating in minimally invasive surgery.

Compared to the above-described drive mechanism using a whiffletree and a polygonal framework for the approximation of a circular movement, the planetary gear has the advantage of being based on a circular movement.

According to a further aspect of the invention, provision is made that, in the non-pivoted position of the end effector, the planet gears and associated ring gear segments can be arranged symmetrically with respect to a center axis of the parallel transmission elements and are movable in opposite directions by control elements engaging jointly on both ring gear segments, in order to generate via the respective planet carriers a unidirectional movement of the transmission elements for opening or closing the end effector by means of rotation of both function units.

By virtue of the symmetrical structure and symmetrical drive movements, both transmission elements can be actuated simultaneously. The gear arrangement according to the invention advantageously has a sufficient rotatability of the pivotable ring gear segments relative to each other. For this purpose, the ring gear segments extend about a circumferential angle of preferably 90° to 155°.

According to a further aspect of the invention, the first drive unit and the second drive unit can be additively coupled via the planetary gear arrangement.

A further advantage of the planetary gear lies in the possibility of setting in motion all of the rotation elements (sun gear, planet gears and ring gear segments), wherein one planet gear can be driven (summing gear) with the two drive units (sun gear and ring gear segments). The planet carriers serving as output members each summate the moments resulting from the drive units, i.e. the torque, if only the sun gear were driven (with fixed ring gear segments), is added to the torque if only the two ring gear segments were driven (with fixed, free-wheeling or supporting sun gear).

In a further advantageous embodiment of the invention, provision is made that at least one of the control elements is provided with a securing device for securing the actuating element in at least one end position and/or one or more intermediate positions.

By the coupling to one or both of the control elements by the securing device, the respective control element can be locked or arrested, such that it does not accidentally move out of place. In addition, with the securing device, it is possible to easily adjust certain functional positions of the two-part end effector of the medical instrument, for example the gripping or opening position of a gripper. By means of securing devices for the control elements or selective disengagement of the drive unit, it is possible for the surgical instrument to be handled safely and in a user-friendly way.

According to a further aspect of the invention, the at least one control element is configured as a lever, joystick or actuation button.

A joystick, actuation button or lever can be formed, for example, at the proximal end region of the shaft as a pivoting mechanism for the medical instrument. Advantageously, grip recesses or grip eyelets are provided for control and, with just one finger or a few fingers, can be used to easily control the pivoting angle and inclination angle of the medical instrument.

According to a further aspect of the invention, the translatory transmission elements are pulling or pushing elements chosen from the group comprising: pull or push rod, press rod, cable pull or combinations thereof.

When cable pulls are used, particularly tight guidance of the cable pulls in the shaft is possible, wherein the outer tube can have a small diameter. The cable pulls can be guided by deflection rollers and/or eyelets and can be combined with rigid thrust elements. The translatory transmission elements convert the pivoting movement of the planet gears abut the axis of the sun gear into an axial movement and, at the distal end of the instrument, in turn convert the axial movement of the transmission elements into the rotation of the function units.

The invention further relates to a surgical instrument which comprises a distally arranged two-part end effector and a proximally arranged handle with a grip part that can be gripped in the hand, and with a gear arrangement having two drive units. Moreover, a shaft is made available which connects the handle to the end effector and has translatory transmission elements in order to pivot or to open or close the two-part distally arranged end effector by means of a respective control element arranged at the handle and by means of an associated drive unit.

The gear arrangement according to the invention in the handle of the surgical instrument are based on the one hand on a whiffletree mechanism and on the other hand on a planetary gear and permit a purely manual, articulated, strong and ergonomic minimally invasive instrument with which it is possible to work with precision.

The present invention will be described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
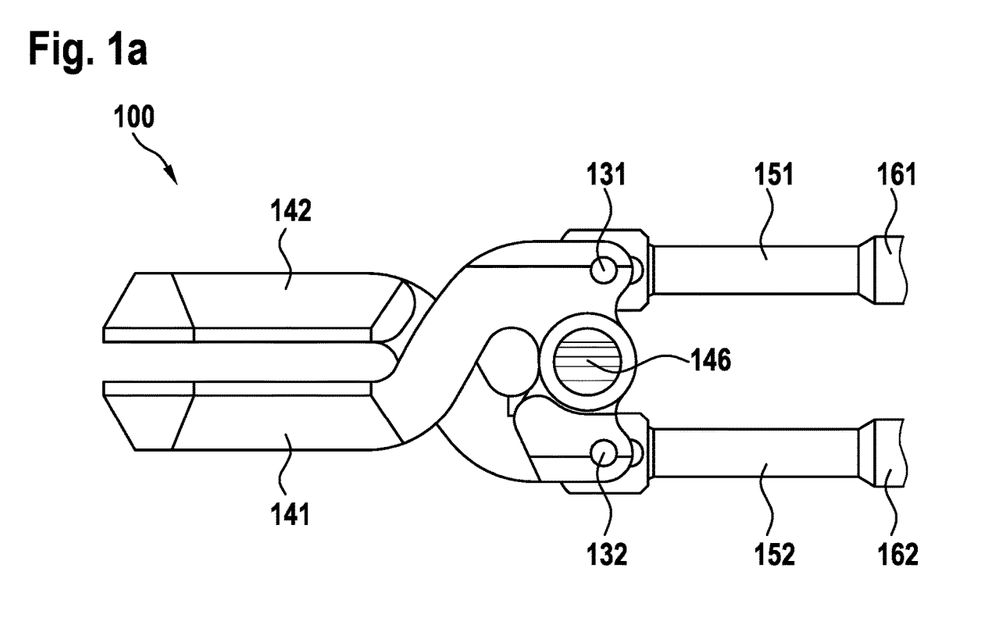
FIG. 1a is a schematic plan view of a head piece of a surgical gripping instrument.

Referring to the drawings, FIG. 1a shows a distal head piece 100 for a medical instrument, with a two-part end effector having two interacting function units 141, 142 that form gripping forceps. For gripping, holding or clamping, the end effector has two distally arranged function units 141, 142, also called jaw parts, which are mounted rotatably about the rotation axis 146 and which are each connected to a respective translatory transmission element 151, 152. The transmission elements 151, 152 are configured as pulling or pushing rods and can actuate the function units 141, 142 individually, i.e. independently of each other. The pulling or pushing rods 151, 152 run through a shaft (not shown in any detail) as far as a distally arranged handle (not shown in FIG. 1).

Each movement of the pulling or pushing rods 151, 152 is transmitted via the joints 131, 132 to the respective jaw parts 142, 141. Moreover, joints 161, 162 are arranged at the distal end of the transmission elements 151, 152 in order to attach at least two drive units. By means of a control element (not shown in any detail), for example with a lever mechanism, manual movements on the part of a person operating the instrument can be transmitted via a drive unit, and via transmission elements 151, 152 connected to the latter, to the effector e.g. dissecting forceps.

Figure 1B:
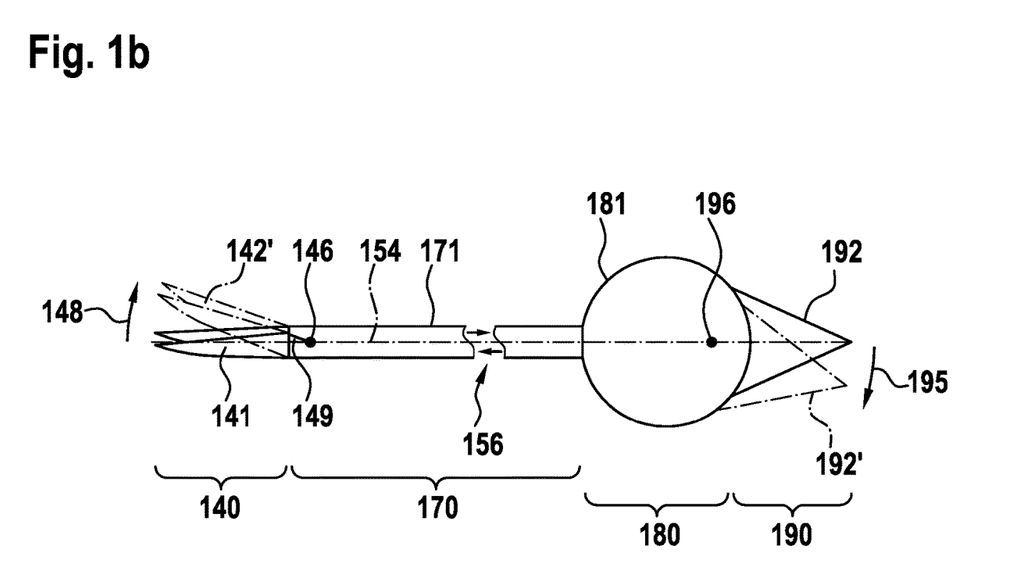
FIG. 1b is a schematic plan view of a surgical cutting instrument with an end effector, which is indicated in a pivoted position by broken lines.

FIG. 1b is a highly schematic representation of a further embodiment of a medical instrument according to the invention, which has a two-part end effector 140, a shaft 170, a handle 180 and a control unit 190. In this embodiment, the end effector 140 is configured in the form of scissors with two cutting blades or jaw parts 141, 142. The outer tube 171 of the shaft 170 is connected to the housing 181. Translatory transmission elements 151, 152 extending parallel to each other in the interior of the shaft 170 can be coupled to two drive units arranged in the housing. Depending on the chosen drive unit, the translatory transmission elements 151, 152 can each generate a positive thrust or pressure or a negative thrust. The thrust can finally be converted into the rotation of a jaw part 141, 142. The transmission elements 151, 152 thus serve to actuate the end effector 140 and can be configured as rods or cable pulls or a combination thereof. When using cable pulls, it is possible for the outer tube 171 to have a small diameter.

Both scissor jaw parts 141, 142 are mounted rotatably about the rotation axis 146 and are shown in FIG. 1b in a partially opened position. A complete closure of the scissor jaw parts can take place by a movement of the jaw parts to each other. Opening or closing is preferably generated by a unidirectional movement of the transmission elements 151, 152 extending in parallel along the longitudinal axis 154 of the shaft 170.

FIG. 1b illustrates a pivoting movement of the end effector 140 in the drawing plane, wherein the jaw parts 141, 142 are pivoted laterally with respect to the longitudinal axis 154 of the shaft 170. The pivoting of both function units or jaw parts 141, 142 of the end effector 140 takes place simultaneously and in the same direction about the pivoting angle 149 with respect to the longitudinal axis 154 of the shaft when the transmission elements 151, 152 are moved in opposite directions, as is indicated by the arrows 156 in FIG. 1b.

FIG. 1b illustrates in particular a pivoting movement of the end effector about a pivoting angle 149. The scissor jaw parts 141', 142' pivoted in the same direction clockwise (see arrow 148) about the rotation axis 146 are shown in a dot-and-dash line superposed on the non-pivoted end effector (jaw parts 141, 142 with solid line and pivoting angle=0°).

A separate control element 192 is made available for the unidirectional pivoting of the scissor jaw parts 141', 142' to a position of the scissor jaw parts 141', 142' inclined relative to the longitudinal axis 154 of the shaft 170. The control element 192 is mounted on the handle 180 in such a way as to be rotatable about a rotation axis 196, which is perpendicular to the longitudinal axis 154, such that the control element 192 is pivotable to both sides with respect to the longitudinal axis 154. For the pivoting of the end effector 140, the control element is rotated from its basic position 192 to the pivoted position 192'. The person operating the instrument can, for example with one or more fingers, control the control element 192 arranged at the end of the handle 180 remote from the end effector. For this purpose, one or more grip recesses can be provided. In addition to a lever, it is also possible to provide a button or joystick lever as the control element.

The pivoted position of the end effector is shown only by way of example. The drive unit arranged in the housing 181 of the handle and used for the pivoting permits simultaneous pivoting of the jaw parts 141, 142 in an angle range of preferably 0° to 90°. If the respective pivoting angle of the pivoting body corresponds to the pivoting angle of the medical instrument, the control element 192 for the pivoting drive can be controlled intuitively. It is moreover advantageous that, in each of the pivoted positions, the jaw parts 141, 142 can be opened or closed by actuation of a further control element of the control unit 190, which further control element cannot be seen in this view.

Figure 2:
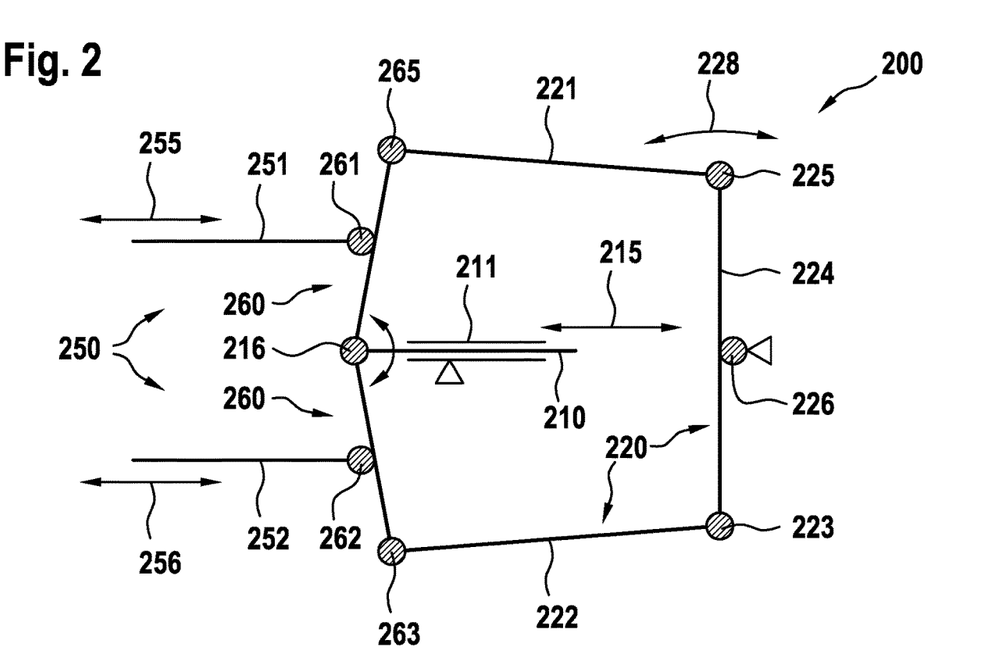
FIG. 2 is a view of an embodiment of a gear arrangement with a whiffletree mechanism.

FIG. 2 shows an embodiment of a gear arrangement 200 for moving a two-part end effector of a surgical instrument. The gear arrangement 200 comprises a whiffletree mechanism which, depending on drive units 210, 220 engaging on the whiffletree 260, transmits a linear movement 215 or a rotation movement 228 to the transmission unit 250.

FIG. 2 shows schematically, as transmission unit 250, the end portions of two translatory transmission elements 251, 252 which are configured as pulling or pushing rods and can each be coupled at the distal ends (not shown) to a function unit of a two-art end effector. A two-part end effector 140 can be, for example, a gripper or scissors, as shown in FIG. 1a or 1b. Moreover, other two-part end effectors such as forceps or applicator forceps for clips, staples or the like can be connected to the distal ends of the transmission elements 251, 252. The pulling or pushing rods 251, 252 can be guided linearly in a shaft (not shown). The linear guiding is illustrated by the respective double arrows 255, 256. At both proximal ends of the transmission elements 251, 252, respective joint connections 261, 262 are provided which operatively connect the whiffletree 260 to the transmission unit 250.

The whiffletree 260 extends substantially transversely with respect to the direction of movement of the transmission elements 251, 252, which are displaceable along the longitudinal axis of the shaft. Arranged centrally between the transmission elements 251, 252 is a first drive unit 210, which is configured as a displaceable thrust element which is guided linearly along a linear bearing 211. The free end of the drive unit 210 can be connected via a lever mechanism to a control element (not shown in any detail), e.g. a pivotable actuating lever. The control element can preferably be configured as a grip part with a grip eyelet for a finger, such that pulling and pushing forces can be applied equally easily with just one finger.

When the control element of the first drive unit 210 is actuated, the thrust element is moved linearly (see double arrow 215) by the pressure or tension applied by the person operating the instrument. This linear movement is transmitted via the whiffletree 260 to both transmission elements 251, 252, such that these move in the same direction with a positive or negative thrust in the longitudinal direction of the shaft. By means of the unidirectional movement of the transmission elements 251, 252, the free ends of the jaw parts of the end effector can be rotated away from each other, in the case of a sliding movement in the direction of the end effector, and can be rotated toward each other, in the case of a sliding movement in the opposite direction. In this way, the end effector can be opened or closed depending on the thrust direction.

In order to bring about a pivoting of the end effector, the whiffletree 260 is connected to a second drive unit 220, the latter comprising a rotation element 224 in the form of a rod which is mounted rotatably about a pivot axis 226. In order to transmit the rotation movement 228 to the whiffletree 260, connection rods 221 and 222 are provided between the respective protruding ends of the whiffletree 260 and the free ends of the rotation element 224. The rods 221, 222, 224 and the whiffletree 260 with an obtuse angle at the center (obtuse angle indicated by the double arrow at joint 216) are connected in an articulated manner via the joints 263, 265 and 225, 223, respectively, and form a polygonal, preferably pentagonal, rod system or framework.

A pivoting movement and rotation of the drive unit 220 about the pivot axis 240 bring about a contradirectional thrust movement of the translatory transmission elements 251 and 252. This differential movement generates, as shown in FIG. 1b, a pivoting of the instrument head with respect to the longitudinal axis. The rotatable drive unit 220 can be configured as a control element, e.g. a grip wheel, or can be brought into engagement with a separate control element (as is indicated schematically in FIG. 1b). As the control element, it is possible, for example, to use a lever mechanism or joystick, which are mounted so as to be pivotable with respect to a handle housing or gear housing (not shown in any detail) and to the instrument shaft.

In the neutral position shown in FIG. 2, the frameworks of the polygon consisting of rods of the drive unit 220 and of the angled whiffletree 260 approximate the circular arc movements of the instrument head. However, it should be noted that, in a pivoted position of the end effector, the opening angle of the end effector is not linear but sinusoidal, depending on the travel of the pushing or pulling rods 251, 252. To avoid this dependency, the following embodiment illustrated in FIG. 3 was developed, with a gear arrangement which is based on a circular movement.

Figure 3:
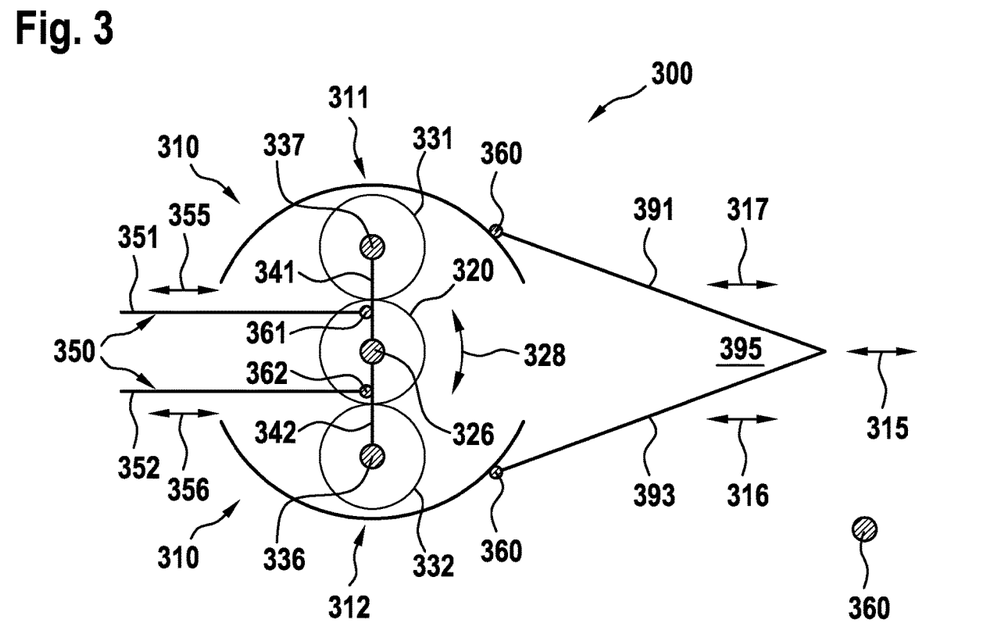
FIG. 3 is a sectional view through a further embodiment of a gear arrangement with a planetary gear transmission mechanism.

FIG. 3 shows a schematic representation of a further embodiment of a gear arrangement 300, which can move at least one function unit of an instrument head by means of a planetary gear mechanism. With the aid of the planetary gear, the gear arrangement 300 according to the invention can convert torques 328 into linear thrust movements 355, 356 of the transmission elements 351 and 352 and, depending on the selected drive unit 310, 320, can bring about an actuation (opening or closing) or pivoting of a two-part end effector. By comparison with an embodiment based on a whiffletree mechanism (see FIG. 2), the use of a planetary gear has the advantage that the gear is based on a circular movement and can function as summing gear.

The planetary gear transmission mechanism of the gear arrangement 300 has a central sun gear 320, which is in engagement with a first planet gear 331 and a second planet gear 332. Each planet gear 331, 332 can be engaged via an outer toothing in an inner toothing of the ring gear segments 311 and 312. The ring gear segments 311 and 312 are ring-shaped or crescent-shaped and can also be designated as first and second ring part or rotation elements 311, 312 of the first drive unit 310. Each ring gear segment 311, 312 can extend over a circumferential angle of preferably 90° to 155° and can be rotated about the rotation axis 326 of the sun gear 320.

In the closed and non-pivoted basic position of the end effector, the planet gears 331, 332 and associated ring gear segments 311, 312 are arranged symmetrically with respect to an imaginary plane of symmetry, which is perpendicular to a center axis of the transmission unit 350 or the longitudinal axis of the shaft (not shown in any detail in FIG. 3). With the aid of the symmetrical configuration of the gear, both translatory transmission elements 351, 352 can be controlled. The upper half of the planetary gear shown in FIG. 3, in particular the planet gear 331 with the planet carrier 341 as output, can transmit linear thrust movements 355 to the upper transmission element 351, whereas the lower half of the gear arrangement can move the lower transmission element 352 linearly (see double arrow 356).

As the driving rotation element for the upper planet gear 331, for example, it is possible to select either the associated ring gear segment 311 of the first drive unit 310 or the sun gear 320 of the second drive unit 320. Respective control elements are provided for moving the rotation elements of the drive units 310 or 320.

As regards the first drive unit 310, control elements 391 and 392 are made available which are each secured via a joint 360 to the outside of a ring gear segment 311 and 312, respectively, and are configured as thrust rods. When the control element 391 is displaced according to the double arrow 317, the upper ring gear segment 311 moves. Thereafter, the planet gear 331, which is at the same time supported on the sun gear 320, rolls in the ring gear segment 311. As has already been explained, the movement of the planet gear 331 is taken up by the associated planet carrier 341 and transmitted to the translatory transmission element 351. In this way, at least one function unit of the end effector can be moved with respect to the other function unit and can thus bring about the closing or opening of the end effector.

According to the same principle, the planet gear 332 can also be moved, wherein a movement 316 of the control element 393 is able to move the ring gear segment 312. The two control elements 391, 393 can advantageously be connected at their proximal end in order to form a control element 395 which, with a single movement 315, can move both thrust rods and thus in each case the rotation elements 311, 312 of the drive unit 310. In this way, the translatory transmission elements 351 and 352 can be moved simultaneously and in the same direction in order to open and close the end effector.

The sun gear 320 serves as second drive unit 320. When the sun gear 320 is rotated about the rotation axis 326 in a direction of the double arrow 328 by means of a control element (not shown in any detail), both planet gears 331, 332 are rotated in the same direction.

Each planet gear 331, 332 is supported on the respective ring gear segment 311, 312 and moves the planet carrier 341, 342 articulated on the respective planet gear rotation axes 337, 336. In this way, a unidirectional movement of the planet carriers 341, 342 about the common rotation axis 326 is generated, as a result of which a contradirectional movement of the transmission elements 351 and 352 is actuated. The joints 361, 362 are used to transmit a positive or negative thrust movement 355, 356 to a translatory transmission element 351, 352, respectively. The contradirectional thrust movements generate a pivoting of an end effector (not shown here).

Figure 4A:
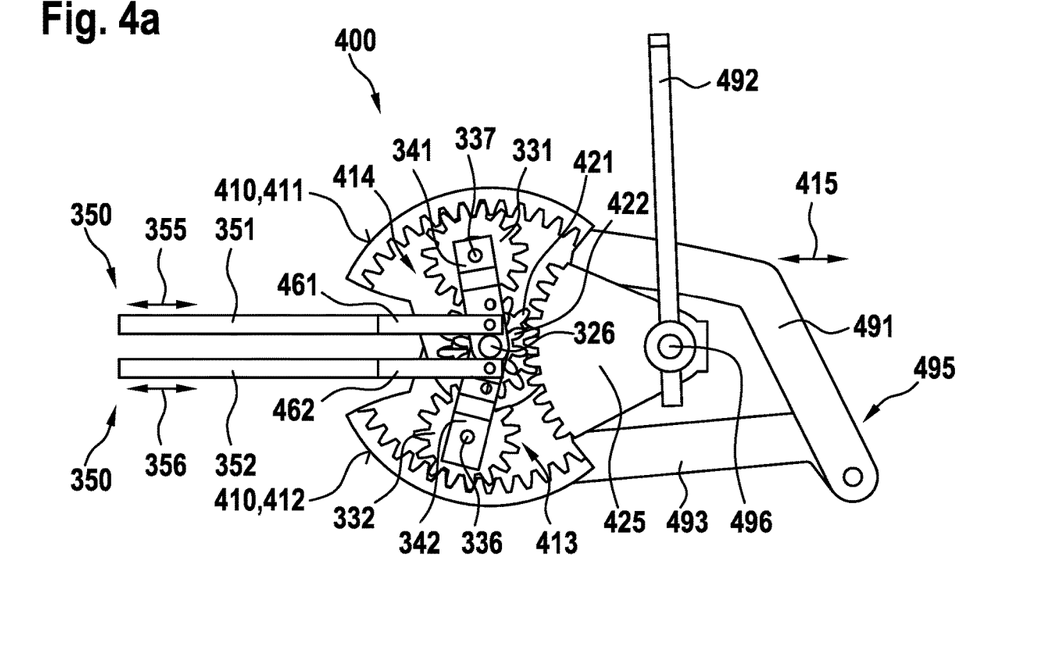
FIG. 4a is a schematic plan view of a further embodiment of the gear arrangement according to the invention based on a planetary gear.
Figure 4B:
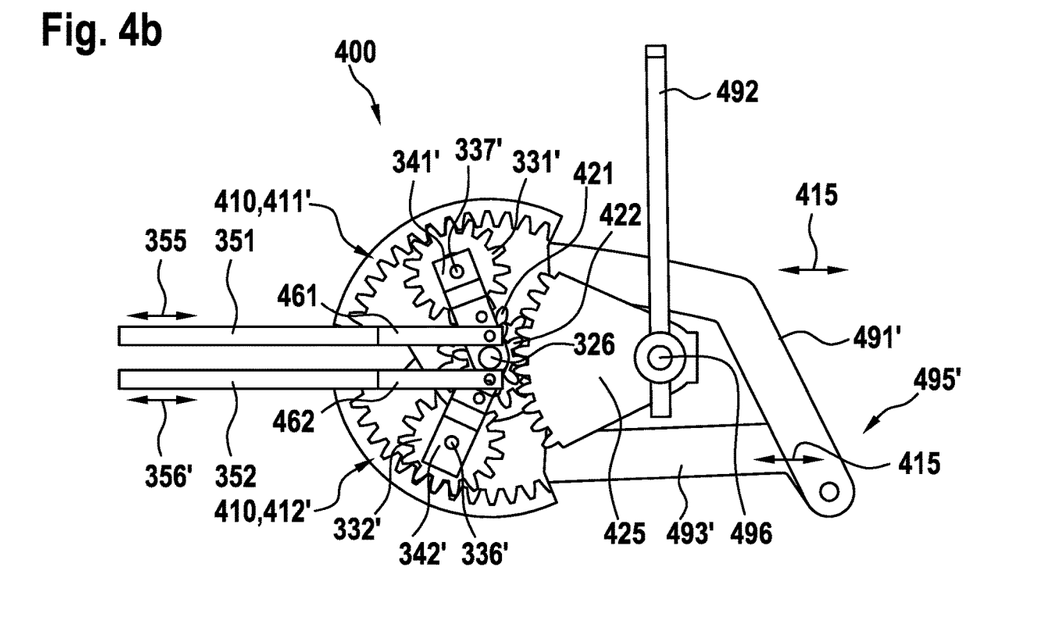
FIG. 4b is a view of the gear arrangement of FIG. 4a after actuation of the control unit for opening or closing an end effector.
Figure 4C:
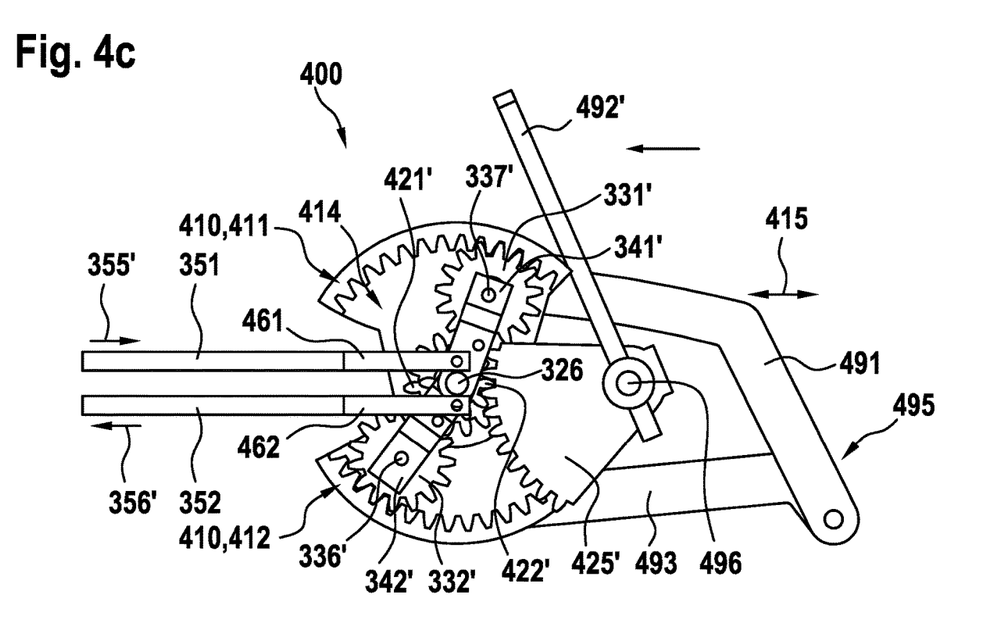
FIG. 4c is a view of the gear arrangement of FIG. 4a after actuation of the control unit for pivoting an end effector.

The way in which a gear arrangement 400 according to the invention functions is shown by way of example on the basis of schematic representations of the planetary gear before and after actuation of the respective drive units 410, 420 in FIGS. 4a, 4b and 4c. The gear arrangement 400 shown in FIG. 4 comprises substantially the same planetary gear mechanism with the planet gears 331, 332 and the planet carriers 341, 342 as output elements, as in the illustrative embodiment 300 shown in FIG. 3. Therefore, the same reference signs are used to designate identical parts. The parts that differ from the above illustrative embodiment 300 are identified with new reference signs.

FIG. 4, in contrast to FIG. 3, shows ring gear segments 411 and 412 with a smaller circumferential angle of approximately 90-95°. Moreover, the ring gear segments 411 and 412 are each arranged on a rotary disk segment 414, 413 mounted rotatably around the sun gear axis 326. The control elements 491 and 493 are mounted on the outside, i.e. on the side directed away from the planet gear. The control element 491 is angled in such a way that it overlaps the free end of the control element 493 and can be connected to the latter in an articulated manner. In this way, both control elements 491, 493 can be operated as a control unit 495 and can be displaced in the direction of the double arrow 415.

Moreover, a control element 492 in the form of a lever pivotable about the rotation axis 496 is made available, which is connected to a gearwheel segment 425. As is shown in FIG. 4a, the outer toothing of the gearwheel segment 425 can be locked at a distance from the outer toothing of the rotation element 332 such that the rotation element 322 and the larger sun gear 321 connected thereto are in freewheel. A further position of the control element is shown in FIG. 4b, wherein the gearwheel segment 425 engages in the teeth of the rotation element 322. This position can advantageously be locked in order to function as a blocking control of the sun gear 321. When the sun gear 322 is fixed in this way, it serves as a support gear for the peripheral planet gears 331, 332. This securing mechanism can be used if the first drive unit 410 is actuated, as is shown in FIG. 4b.

FIGS. 4a and 4b are schematic representations of the gear arrangement 400 before and after actuation of the first drive unit 410. The first drive unit 410 is configured for opening and closing a distally arranged end effector, wherein a unidirectional movement of the transmission elements 351, 352 and hence a contradirectional movement of the rotatable function units of the end effector can be brought about. For this purpose, the control element 495 or the two control units 491 and 493 are displaced at the same time in the direction of the transmission unit 350. The displaced control elements 491', 493' are shown in FIG. 4b, and also the rotated ring gear segments 411' and 412'. The planet gear 331' is moved with the counterclockwise rotated ring gear segment 411' and thus shifts its rotation axis 336', and the end of the planet carrier 341 articulated thereon, in the direction of the transmission unit 350. Similarly, the clockwise rotated planet gear 332' takes up the drive force transmitted by the ring gear segment 412' and transmits this to the coupled planet carrier 342. The coupling elements 461, 462 are configured as a stable sleeve extending in the longitudinal direction and can each convert the movement of the planet carriers 341, 342 into unidirectional translatory movements 355, 356 of the transmission elements 351 and 352.

FIG. 4c shows the gear arrangement when the second control element 493 and thus the second drive unit in the form of a sun gear 421 is actuated. The second drive unit or the sun gear 421 is configured for pivoting a distally arranged end effector, wherein a contradirectional movement 355', 356' of the transmission elements 351, 352 and hence a unidirectional movement of the rotatable function units of the end effector can be brought about. To pivot an end effector, the sun gear 421 is used as drive unit 320, such that in this configuration the ring gear segments 411, 412 serve only for support. For the rotation of the sun gear 421, the gearwheel segment 425' is pivoted counterclockwise by means of the control element or pivoting lever 492 and thereby engages in the teeth of the rotation element 422'. This generates a clockwise rotation movement of the rotation element 422' and therefore of the coaxially mounted sun gear 421'. The movement of the sun gear 421' is transmitted to both planet gears 331' and 332', wherein the rotation axis 337' is moved away from the transmission unit, while the rotation axis 336' is moved toward the transmission unit 350. In this way, the transmission elements 351, 352 are moved in opposite directions 355', 356' and thereby generate a pivoting of the end effector.

The embodiments of the gear arrangement according to the invention and of a surgical maneuvering device, described above and shown in the figures, can be used in all fields of medicine and in particular in endoscopy. Its use in minimally invasive surgery is particularly preferred. However, the present invention can also be used for other applications, for example technical inspections of cavities.

A gear arrangement is made available which two drive units 210, 220, 310, 320, 410, and two translatory transmission elements 151, 152, 251, 252, 351, 352, to each of which a rotationally movable function unit 141, 142 of a distally arranged two-part end effector 140 can be coupled. The first drive unit 210, 310, 410 has at least one proximally arranged rotation element 311, 411 or a thrust element 210 for opening or closing the end effector 140 by means of rotation of at least one function unit 141, 142. The second drive unit 220, 320, with which the translatory transmission elements 151, 152, 251, 252, 351, 352 are movable in opposite directions, has at least one proximally arranged rotation element 224, 320, 421 for simultaneous and unidirectional pivoting of the function units 141, 142 of the end effector 140. The present invention further relates to a surgical instrument with said gear arrangement 200, 300, 400 in the handle 180. The gear arrangement 200, 300, 400 according to the invention for a surgical instrument is based, on the one hand, on a whiffletree mechanism and, on the other hand, on a planetary gear and can be controlled by means of two control elements 191, 192, 391, 393, 491, 492, 493 assigned to the drive units 210, 220, 310, 320, 410.

While specific embodiments of the invention have been shown and described in detail to illustrate the application of the principles of the invention, it will be understood that the invention may be embodied otherwise without departing from such principles.

What is claimed is:

1. A gear arrangement for a surgical instrument, the gear arrangement comprising:
    two drive units; and
    two translatory transmission elements, wherein a distally arranged two-part end effector comprises a plurality of function units, each of the function units being configured to be coupled to one of the two translatory transmission elements, wherein a first drive unit of the two drive units has at least one proximally arranged rotation element or a thrust element for opening and closing the two-part end effector by rotation of at least one of the plurality of function units, wherein a second drive unit of the two drive units has at least one proximally arranged rotation element for simultaneous and unidirectional pivoting of the plurality of function units of the two-part end effector, wherein the translatory transmission elements are movable in opposite directions via the second drive unit, wherein the translatory transmission elements are movable in the same direction via the first drive unit, wherein the at least one proximally arranged rotation element of the second drive unit is configured as a sun gear that can be driven in rotation, wherein a first planet gear and a second planet gear for taking up a drive torque is in constant toothed engagement with the sun gear and resulting movements of the first planet gear and the second planet gear can be conveyed to respective first and second planet carriers, wherein each of the two translatory transmission elements is coupled to the respective first and second planet carriers in order to be movable in opposite directions during rotation of the sun gear.

2. A gear arrangement according to claim 1, wherein the sun gear is configured to be driven in rotation directly or indirectly via a further coaxially arranged rotation element connected fixedly to the sun gear, wherein the sun gear is selectively in toothed engagement with an outer toothing of a pivotable gearwheel segment of a control element.

3. A gear arrangement according to claim 2, wherein the at least one proximally arranged rotation element of the first drive unit comprises two rotation elements, wherein a first rotation element of the two rotation elements is configured as a first ring gear segment that can be driven in rotation, wherein the first planet gear for taking up a drive torque is in constant toothed engagement with the first ring gear segment and resulting movements of the first planet gear are conveyed to the first planet carrier, wherein an output of the first planet carrier is converted by a first transmission element of the two transmission elements, according to a chosen direction of drive rotation of the first ring gear segment, into a positive or negative thrust for opening or closing the two-part end effector by rotation of a first function unit of the plurality of function units.

4. A gear arrangement according to claim 3, wherein a second rotation element of the two rotation elements is configured as a second ring gear segment, wherein the second planet gear for taking up a drive torque is in constant toothed engagement with the second ring gear segment, and movement of the second planet gear is conveyed to the second planet carrier, wherein a second transmission element of the two translatory transmission elements is coupled to the second planet carrier and converts an output of the second planet carrier, according to the chosen direction of drive rotation of the second ring gear segment, into the positive or negative thrust for opening or closing the two-part end effector by rotation of a second function unit of the plurality of function units.

5. A gear arrangement according to claim 4, wherein, in a non-pivoted position of the two-part end effector, the first planet gear and the second planet gear and the associated first and second ring gear segments are configured to be arranged symmetrically with respect to a center axis of the translatory transmission elements and are movable in opposite directions by the control element engaging jointly on the first and second ring gear segments, in order to generate via the respective first and second planet carriers a unidirectional movement of one of the two translatory transmission elements for opening and closing the two-part end effector by rotation of the plurality of function units.

6. A gear arrangement according to claim 1, wherein at least one control element has a securing device for securing the at least one control element in at least one of at least one end position and one or more intermediate positions.

7. A gear arrangement according to claim 1, wherein at least one control element is configured as one of a lever, a joystick and an actuation button.

8. A gear arrangement according to claim 1, wherein the two translatory transmission elements are pulling or pushing elements comprising one or more of a pull or push rod, a press rod and a cable pull.

9. A gear arrangement according to claim 1, wherein the translatory transmission elements between the two-part end effector and the two drive units are arranged in an elongated shaft, wherein a handle is arranged at a proximal end of the elongated shaft, the handle comprising at least one control element assigned to one of the two drive units.

10. A gear arrangement according to claim 1, wherein the plurality of function units of the two-part end effector is one or more of grippers, scissors, a clamp, a jaw part, an expander, applicator forceps jaw for clips or staples and combinations of grippers, scissors, a clamp, a jaw part, an expander, and applicator forceps jaw for clips or staples.

11. A surgical instrument, comprising:
    a distally arranged two-part end effector;
    a gear arrangement comprising two drive units and two translatory transmission elements, wherein the distally arranged two-part end effector comprises a plurality of function units, each of the function units being coupled to one of the two translatory transmission elements, wherein a first drive unit of the two drive units has at least one proximally arranged rotation element or a thrust element for opening and closing the two-part end effector by rotation of at least one of the plurality of function units, wherein a second drive unit of the two drive units has at least one proximally arranged rotation element for simultaneous and unidirectional pivoting of the plurality of function units of the two-part end effector, wherein the translatory transmission elements are movable in opposite directions via the second drive unit, wherein the translatory transmission elements are movable in the same direction via the first drive unit, wherein the at least one proximally arranged rotation element of the second drive unit is configured as a sun gear that can be driven in rotation, wherein a first planet gear and a second planet gear for taking up a drive torque is in constant toothed engagement with the sun gear and resulting movements of the first planet gear and the second planet gear can be conveyed to respective first and second planet carriers, wherein each of the two translatory transmission elements is coupled to the respective first and second planet carriers in order to be movable in opposite directions during rotation of the sun gear;

a proximally arranged handle with the gear arrangement and a grip part that is configured to be gripped in a hand; and a shaft connecting the handle to the two part end effector and the shaft comprising the two translatory transmission elements in order to pivot or to open and close the two-part end effector by a respective control element arranged at the handle.

* * * * *